US011570562B2

(12) United States Patent
Mitra (10) Patent No.: US 11,570,562 B2
(45) Date of Patent: Jan. 31, 2023

(54) HEARING ASSISTANCE DEVICE FITTING BASED ON HEART RATE SENSOR

(71) Applicant: Starkey Laboratories, Inc., Eden Prairie, MN (US)

(72) Inventor: Tirtha Mitra, Plymouth, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 223 days.

(21) Appl. No.: 17/247,657

(22) Filed: Dec. 18, 2020

(65) Prior Publication Data

US 2021/0195353 A1    Jun. 24, 2021

Related U.S. Application Data

(60) Provisional application No. 62/950,050, filed on Dec. 18, 2019.

(51) Int. Cl.
*H04R 25/00* (2006.01)
*A61B 5/024* (2006.01)
*A61B 5/00* (2006.01)
*G08B 3/10* (2006.01)

(52) U.S. Cl.
CPC .......... *H04R 25/70* (2013.01); *A61B 5/02438* (2013.01); *A61B 5/6817* (2013.01); *A61B 5/6843* (2013.01); *G08B 3/10* (2013.01); *H04R 25/554* (2013.01); *H04R 25/558* (2013.01); *H04R 25/603* (2019.05); *H04R 25/604* (2013.01); *A61B 5/024* (2013.01); *A61B 2562/222* (2013.01); *H04R 2225/023* (2013.01); *H04R 2225/55* (2013.01); *H04R 2225/61* (2013.01)

(58) Field of Classification Search
CPC .......... A61B 2562/222; A61B 5/02438; A61B 5/6817; A61B 5/6843; A61B 5/024; G08B 3/10; H04R 2225/023; H04R 2225/55; H04R 2225/61; H04R 25/554; H04R 25/558; H04R 25/603; H04R 25/604; H04R 25/70; H04R 2225/025
USPC ........................................................ 600/300
See application file for complete search history.

(56) References Cited

U.S. PATENT DOCUMENTS

2022/0225887 A1* 7/2022 Goldman .............. A61B 5/7475

FOREIGN PATENT DOCUMENTS

EP                3840410 A1 *  6/2021  ........... A61B 5/0022

* cited by examiner

*Primary Examiner* — Phylesha Dabney
(74) *Attorney, Agent, or Firm* — Schwegman Lundberg & Woessner, P.A.

(57) ABSTRACT

A heart rate sensor within a hearing assistance device may provide heart rate information or other sensor data, which may be used to determine how well the hearing assistance device fits the patient's ear. The heart rate sensor data provides quantitative feedback that indicates how well the hearing assistance device fits the patient's ear. The heart rate sensor data may be used to provide an indication to the patient to reseat or otherwise adjust the fitting of the hearing assistance device. The improved fitting process provides the ability for the audiologist and patient to identify a preferred or optimized hearing assistance device geometry. This improved fit provides improved performance and reliability of the hearing assistance device.

20 Claims, 4 Drawing Sheets

HEARING ASSISTANCE DEVICE FITTING BASED ON HEART RATE SENSOR

CROSS-REFERENCE TO RELATED APPLICATION

This patent application claims the benefit of U.S. Provisional Patent Application No. 62/950,050, filed Dec. 18, 2019, which is incorporated by reference herein in its entirety.

TECHNICAL FIELD

Embodiments described herein generally relate to hearing assistance device fitting.

BACKGROUND

Hearing assistance devices may include hearing aids, such as behind-the-ear (BTE), in-the-ear (ITE), in-the-canal (ITC), receiver-in-canal (RIC), completely-in-the-canal (CIC), or other types of hearing aids. To improve hearing assistance device performance, an audiologist may provide a custom fitting of the hearing assistance device for the patient (e.g. user). The fitting may include determining a hearing assistance device size, an RIC cable length, a CIC device molding, or other patient customization. However, even with customization, the fitting of a hearing assistance device may change throughout a day, thereby modifying or reducing the hearing assistance device performance. It is desirable to improve hearing assistance device fitting and performance to provide consistent and reliable performance throughout the device lifetime.

DESCRIPTION OF EMBODIMENTS

A heart rate sensor within a hearing assistance device provides technical solutions to address technical problems facing hearing assistance device fitting. The heart rate sensor may provide heart rate information or other sensor data, which may be used to determine how well the hearing assistance device fits the patient's ear. To address technical problems during initial hearing assistance device fitting sessions, such as relying on qualitative patient feedback regarding how well a hearing assistance device seems to be fitting, the heart rate sensor data provides quantitative feedback that indicates how well the hearing assistance device fits the patient's ear. To address technical problems facing ongoing hearing assistance device fittings, such as the fitting of a hearing assistance device changing throughout a day, the heart rate sensor data may be used to provide an indication to the patient to reseat or otherwise adjust the fitting of the hearing assistance device. The improved fitting process provides the ability for the audiologist and patient to identify a preferred or optimized hearing assistance device geometry. This improved fit provides improved performance and reliability of the hearing assistance device. For example, improving the performance of heart rate sensor data collection improves the performance of quantitative heart rate analysis applications (e.g., heart rate monitoring), and improves performance of qualitative heart rate analysis (e.g., a patient comparing hearing assistance detected heart rate against a wearable fitness device detected heart rate). Additional technical advantages provided by analysis of the heart rate sensor within a hearing assistance device are described herein.

This description of embodiments of the present subject matter refers to subject matter in the accompanying drawings, which show, by way of illustration, specific aspects and embodiments in which the present subject matter may be practiced. These embodiments are described in sufficient detail to enable those skilled in the art to practice the present subject matter. References to "an," "one," or "various" embodiments in this disclosure are not necessarily to the same embodiment, and such references contemplate more than one embodiment. The above detailed description is demonstrative and not to be taken in a limiting sense. The scope of the present subject matter is defined by the appended claims, along with the full scope of legal equivalents to which such claims are entitled.

Figure 1:
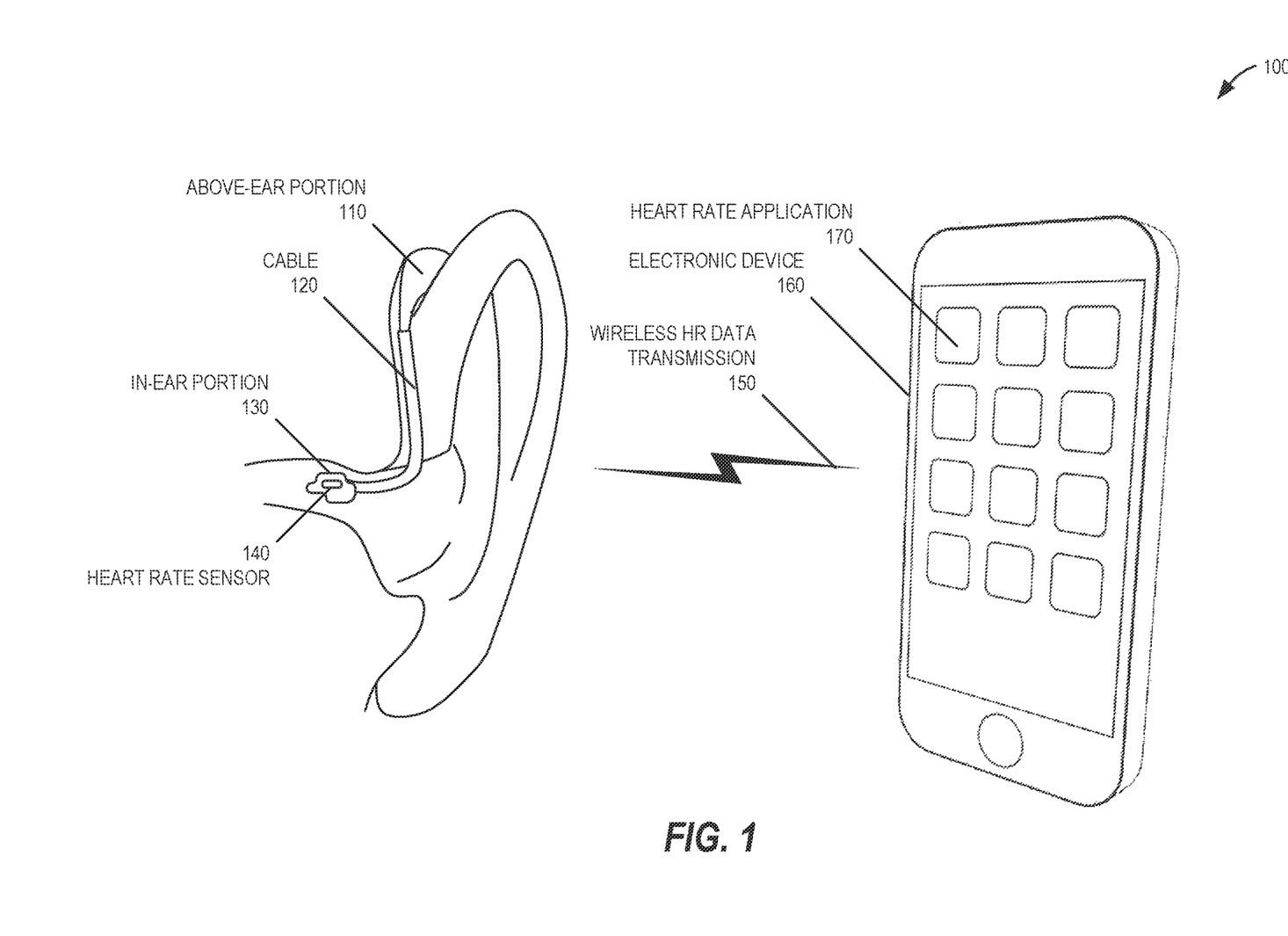
FIG. 1 is hearing assistance device system, in accordance with at least one embodiment of the invention.

FIG. 1 is hearing assistance device system 100, in accordance with at least one embodiment of the invention. System 100 may include a generalized "one size fits all" (e.g., "one size fits most") hearing assistance device receiver, which may include a hearing assistance device above-ear portion 110, a cable portion 120, and an in-ear portion 130. In various embodiments, one or more heart rate sensors 140 may be included within the above-ear portion 110, and the in-ear portion 130. The heart rate sensor 140 may be incorporated anywhere within the in-ear portion 130, provided that the heart rate sensor 140 will be adjacent to or sufficiently close to the skin of the patient to sense heart rate information. The inclusion of a heart rate sensor 140 within one or more portions of a hearing assistance device may be used to detect the use of one or more systems or methods described herein.

The heart rate sensor 140 may be used to provide one or more heart rate sensor signal outputs. The heart rate sensor signal outputs may be used to determine how well the hearing assistance device fits the patient. In an example, one or more of the heart rate sensor signal outputs may be transmitted via a wireless heart rate data transmission 150 to an electronic device 160 for analysis of the transmitted heart rate sensor signal outputs, such as on a heart rate application 170. The electronic device 160 may include a mobile electronic device (e.g., a smartphone), a desktop PC, a cloud software-as-a-service, or other electronic device 160. In an example, one or more of the heart rate sensor signal outputs may be analyzed on the hearing assistance device itself.

In addition to using heart rate sensor signal outputs to determine how well the hearing assistance device fits the patient, the outputs may be used to determine whether a different type of hearing assistance device may be more suitable for the patient. In an example, the heart rate sensor signal outputs may be used to determine whether the patient would be a suitable candidate for a hearing assistance device that included the heart rate sensor 140 within the in-ear portion 130 of a standard snap-fit RIC cable. The heart rate sensor signal outputs may be used to determine whether the patient may be eligible for a generalized "one size fits all" hearing assistance device geometry. For example, a generalized hearing assistance device geometry may be identified when heart rate sensor signal outputs indicate a good fit between the patient and a one size fits all hearing assistance device. Additionally, the heart rate sensor signal outputs may be used to determine the location of the heart rate sensor 140 that would provide the most benefit to the patient, such as selecting a hearing assistance device that included one or more heart rate sensors 140 within the above-ear portion 110, or the in-ear portion 130.

The heart rate sensor signal outputs may include a heart rate indication, such as the number of heart beats per minute, an electrocardiogram (e.g., EKG, ECG) data, or other cardiological data. Accuracy of heart rate sensor data may be affected by the position of the heart rate sensor 140 inside the ear, and by how well the in-ear portion 130 fits within the patient's ear. For example, a particular geometry of the in-ear portion 130 may fit well for some patients, but may not provide accurate heart rate data for other patients with different ear canal geometries or with heart rate sensor-occluding features (e.g., hair, tattoos). The heart rate sensor signal outputs may include heart rate metadata characterizing the heart rate data, and the heart rate metadata may be used to reduce or minimize heart rate data inaccuracies. The heart rate sensor signal outputs may include heart rate metadata characterizing the heart rate data, such as sensor signal quality, a sensor DC value, and other heart rate metadata. The heart rate metadata may be used separately from or in conjunction with heart rate sensor data to determine the quality of heart rate sensor data or to characterize the fit of the hearing assistance device. For example, data from the heart rate sensor 140 may also be affected by irregularities in a patient's heart rate while the patient is sedentary or moving. Heart rate metadata may be used to confirm a correct fitting of the hearing assistance device despite an indication of unusual heart rate sensor data.

Figure 2:
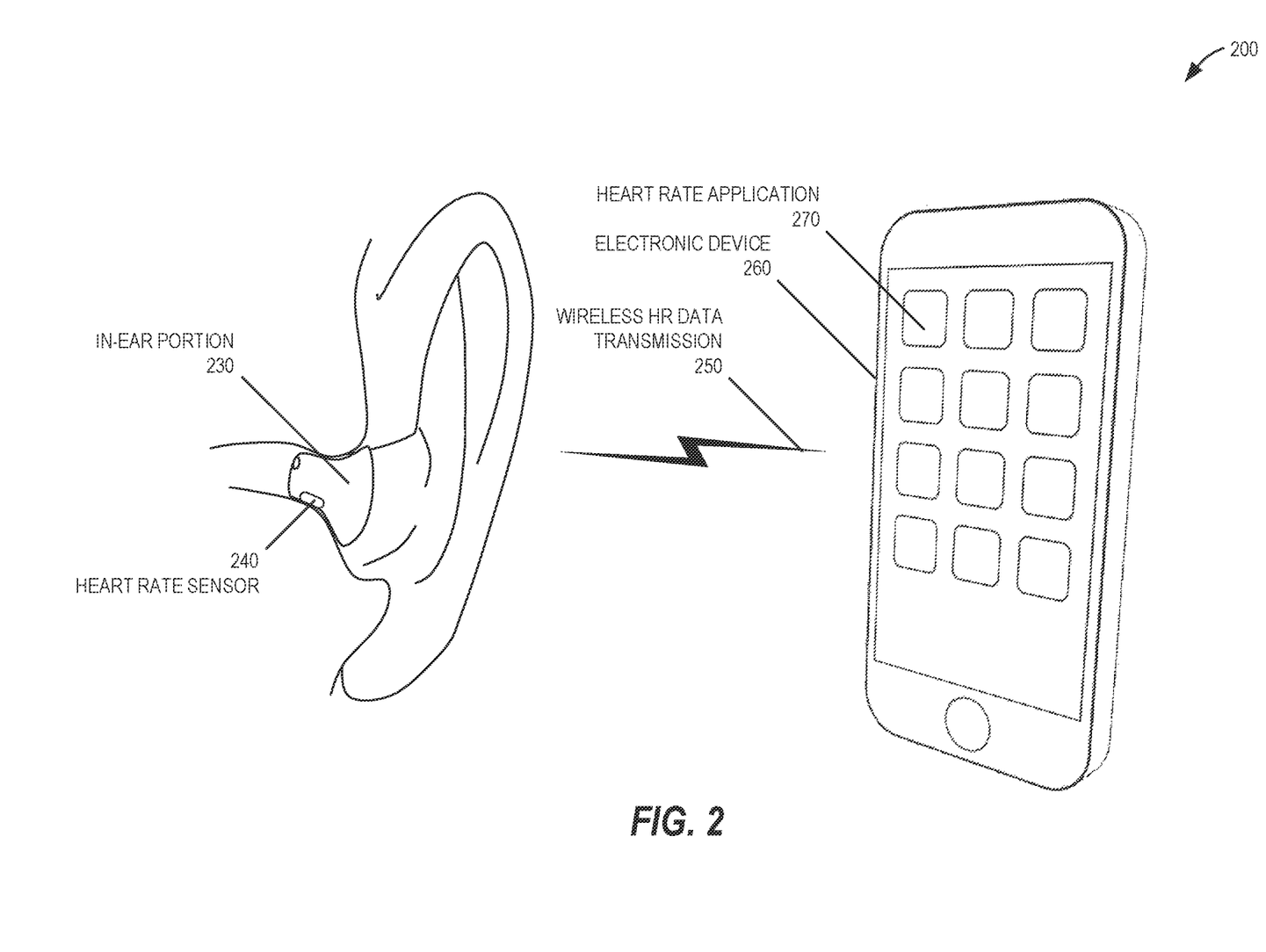
FIG. 2 is hearing assistance device system, in accordance with at least one embodiment of the invention.

FIG. 2 is hearing assistance device system 200, in accordance with at least one embodiment of the invention. System 200 may include a heart rate sensor 240 within an in-ear portion 230, where the in-ear portion 230 may include a custom earmold that is unique to each hearing assistance device patient. One or more of the heart rate sensor signal outputs generated by the heart rate sensor 240 may be analyzed on the hearing assistance device itself, or may be transmitted via a wireless heart rate data transmission 250 to an electronic device 260 for analysis of the transmitted heart rate sensor signal outputs. When the heart rate sensor signal outputs indicate a poor fit, the audiologist or patient may try one or more alternate hearing assistance devices with various geometries to identify a hearing assistance device with an improved fit. In an example, the audiologist may take a new ear impression of the patient's ear and generate a new custom earmold to provide a better fit for the patient.

Diverse types of feedback may be generated for the patient or audiologist. The feedback may include audible feedback generated and provided to the patient, to the audiologist, or to other devices or people. In an example, the feedback may include audible feedback that is transduced at the in-ear portion 230 directly to the patient. In an example, feedback may be provided at the electronic device 260, such as by providing audible or text-based feedback instructions within a mobile device application 270. In an example, feedback may be provided to more than one device, such as by providing audible feedback transduced at the in-ear portion 230 while providing the audiologist a visual indication of the feedback on an electronic device. The feedback, hearing assistance device information, and other device or patient data may be sent to a remote server for further analysis, such as de-identification and data aggregation of patient ear geometries, hearing assistance device geometries, heart rate sensor fitting appointment outcomes, and other audiological analyses. The offering of a hearing assistance device mobile device application 270 (e.g., within an app store) that detects or analyzes heart rate may be used to detect the use of one or more systems or methods described herein.

In an example, one or more of the heart rate sensor signal outputs may be used within the hearing assistance device to provide an initial analysis of the fit of the hearing assistance device, and an audible feedback may be generated to prompt the patient or the audiologist to reseat or otherwise readjust the hearing assistance device. The patient or the audiologist may be prompted to conduct one or more adjustments or activities to improve the fitting analysis. For example, the feedback may prompt the user to sit, stand, walk, jog, bend over, or undertake other physical activities. The heart rate sensor signal outputs may be used to determine whether the hearing assistance device provides a good fit for each of these various activities, and whether a different hearing assistance device geometry may be recommended. In an example, an indication of a poor fit may prompt the user to reseat or otherwise readjust the hearing assistance device and perform additional activities to confirm the indication of a poor fit. This use of a secondary confirmation of a poor fit may improve the reliability of the fit determination, and may improve the recommendation accuracy for a different hearing assistance device geometry. The heart rate sensor signal outputs may be used to recommend a particular hearing assistance device geometry, such as by comparing fit performance of two or more hearing assistance devices throughout various activities. The two or more hearing assistance devices may be compared in pairs (e.g., a first pair followed by a second pair), or may be compared simultaneously (e.g., a pair that includes two different geometries). By comparing multiple existing generalized hearing assistance device geometries (e.g., multiple "one size fits all" devices), a patient or audiologist may be able to select the best fitting hearing assistance device, which may improve the speed and reliability of selection of a hearing assistance device. These types of feedback for the patient or audiologist may be generated on the mobile device or hearing assistance devices shown in or FIG. 1 or FIG. 2. In an example, the heart rate sensor signal outputs may indicate that a custom earmold (e.g., FIG. 2) is better suited for the patient than a one size fits all geometry (e.g., FIG. 1).

Figure 3:
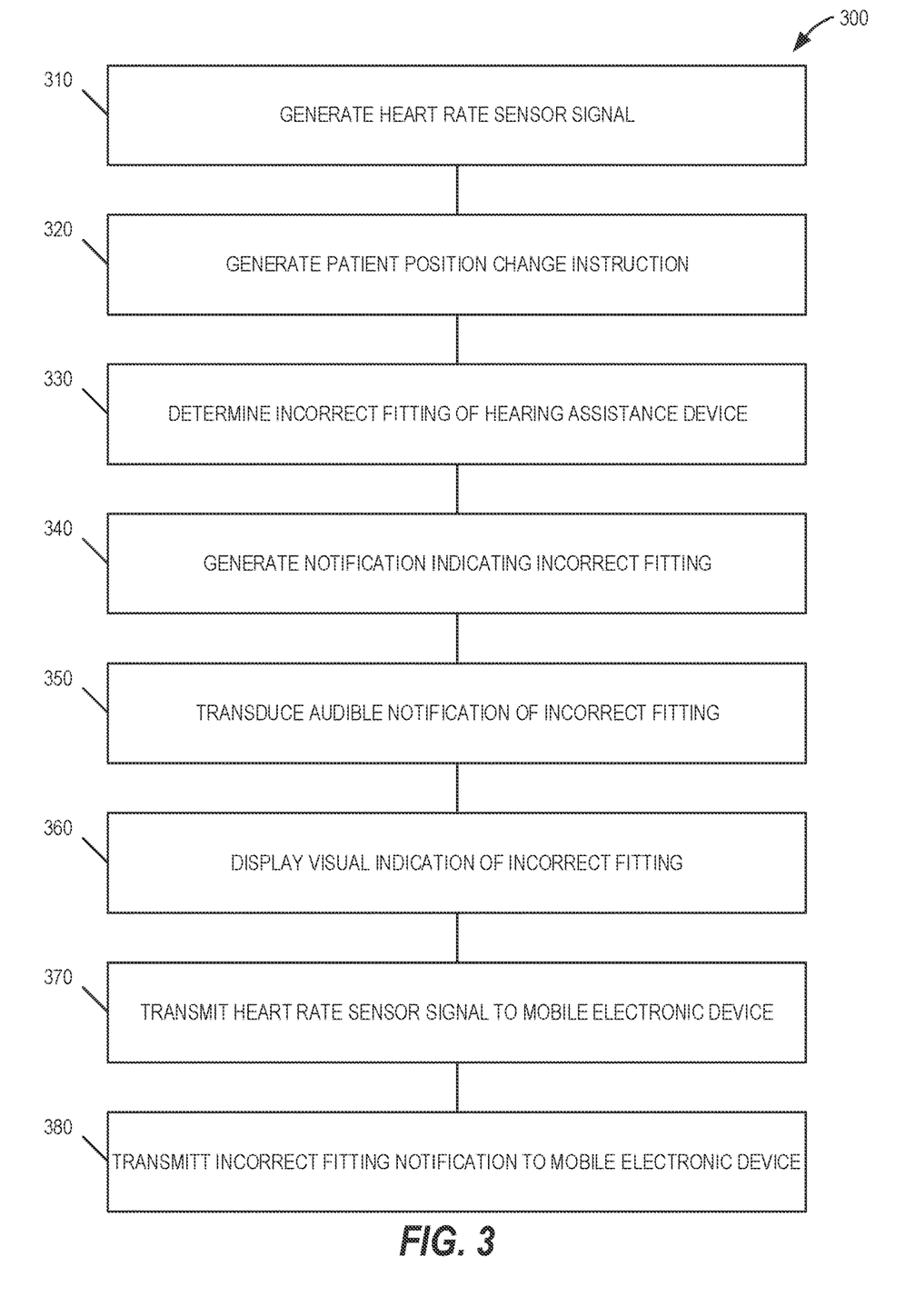
FIG. 3 is a hearing device fitting method, in accordance with at least one embodiment of the invention.

FIG. 3 is a hearing device fitting method 300, in accordance with at least one embodiment of the invention. Method 300 includes generating 310 a heart rate sensor signal of a patient. The heart rate sensor signal may be generated by a heart rate sensor disposed within or otherwise supported by a hearing assistance device. The hearing assistance device may include an in-ear portion, and the heart rate sensor may be attached to the in-ear portion. The in-ear portion may include a "one size fits all" geometry or a custom earmold. The hearing assistance device may include an above-ear portion, and the heart rate sensor may be attached to the above-ear portion.

Method 300 may include generating 320 a patient position change instruction. The position change instruction may include one or more sitting commands, standing commands, walking commands, or other single or sequential instructions for the patient to change positions one or more times. The position change instruction may improve the reliability of the data provided by the heart rate sensor signal, such as by providing sensor data from multiple patient positions or patient activities. The position change instruction may be provided to the user by transducing an audible instruction through the hearing assistance device in-ear portion, by displaying a visual instruction through a mobile application, or otherwise provided to the patient.

Method 300 may include determining 330 an incorrect fitting of the hearing assistance device based on the heart rate sensor signal. The heart rate sensor signal may include a heart rate indication, and the determination of the incorrect fitting may be based on a detected irregularity in the heart rate indication or from the heart rate metadata. The heart rate sensor signal further may include a skin contact flag, and the determination of the incorrect fitting may be based on a detected insufficient contact in the skin contact flag. The heart rate sensor signal further may include at least one of a signal quality and an optical DC value.

Method 300 may also include generating 340 a notification indicating the incorrect fitting of the hearing assistance device. Method 300 may include transducing 350 an audible notification to the patient. Method 300 may include displaying 360 a visual indication of the notification indicating the incorrect fitting of the hearing assistance device. The visual notification may be displayed on a device display of a mobile electronic device external to the hearing assistance device.

In an example, method 300 includes transmitting 370 the heart rate sensor signal from the hearing assistance device to the mobile electronic device. Processing the heart rate sensor signal may be executed on the mobile electronic device, including determining 330 the incorrect fitting based on the heart rate sensor signal and generating 340 the notification indicating the incorrect fitting of the hearing assistance device. In another example, the hearing assistance device may handle processing the heart rate sensor signal, including determining 330 the incorrect fitting of the hearing assistance device, generating 340 the incorrect fitting notification, and transmitting 380 the incorrect fitting notification from the hearing assistance device to the mobile electronic device. One or more of the hearing assistance device and a mobile device may be used to repeat one or more steps within method 300, including generating an additional patient position change instruction and generating additional fitting notifications in response to the initial determination 330 of the incorrect fitting.

Figure 4:
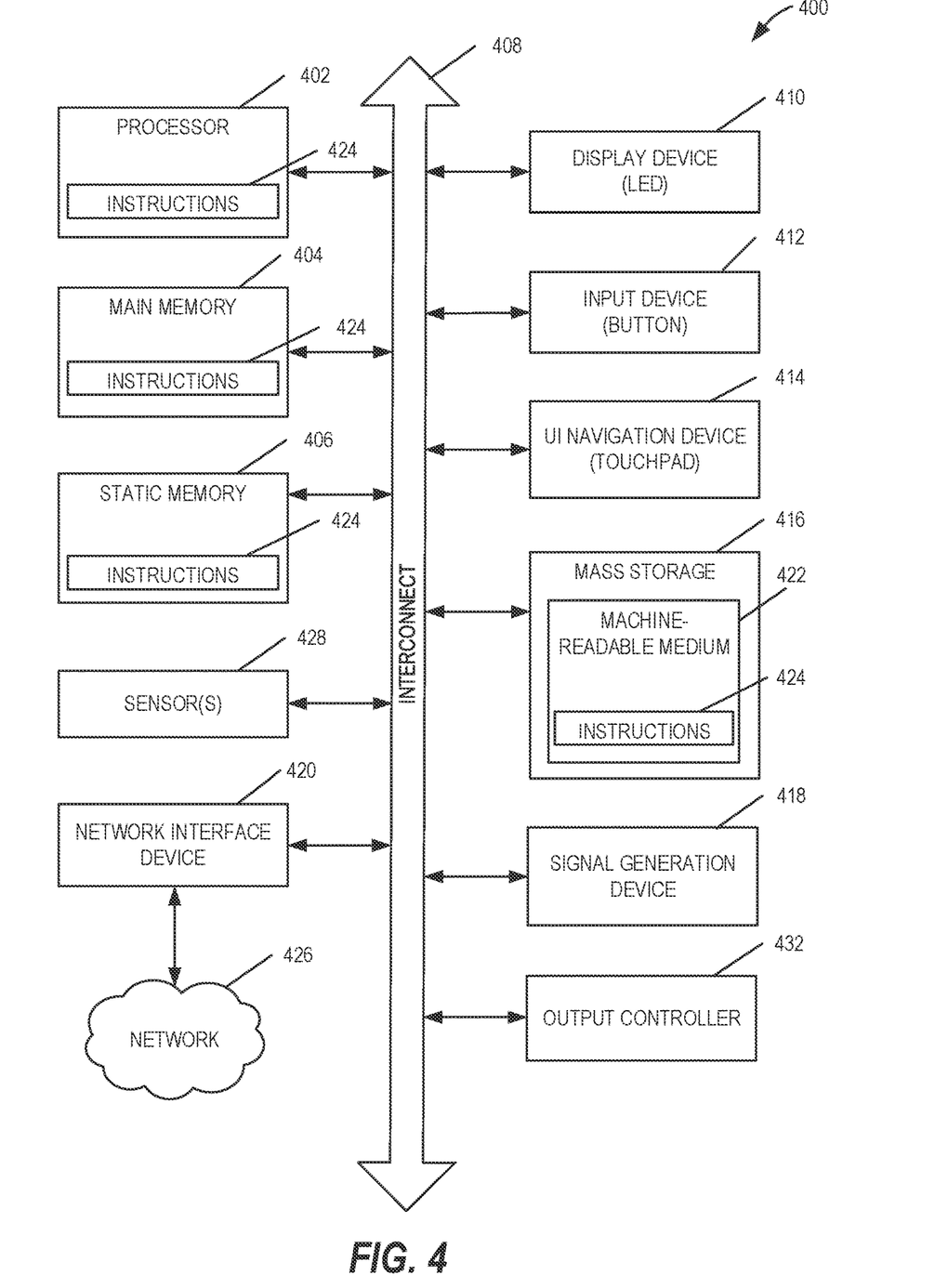
FIG. 4 illustrates a block diagram of an example machine upon which any one or more of the techniques discussed herein may perform.

FIG. 4 illustrates a block diagram of an example machine 400 upon which any one or more of the techniques (e.g., methodologies) discussed herein may perform. In alternative embodiments, the machine 400 may operate as a standalone device or may be connected (e.g., networked) to other machines. In a networked deployment, the machine 400 may operate in the capacity of a server machine, a client machine, or both in server-client network environments. In an example, the machine 400 may act as a peer machine in peer-to-peer (P2P) (or other distributed) network environment. The machine 400 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 400 may include a hardware processor 402 (e.g., a central processing unit (CPU), a graphics processing unit (GPU), a hardware processor core, or any combination thereof), a main memory 404 and a static memory 406, some or all of which may communicate with each other via an interlink (e.g., bus) 408. The machine 400 may further include a display unit 410, an alphanumeric input device 412 (e.g., a keyboard), and a user interface (UI) navigation device 414 (e.g., a mouse). In an example, the display unit 410, input device 412 and UI navigation device 414 may be a touch screen display. The machine 400 may additionally include a storage device (e.g., drive unit) 416, a signal generation device 418 (e.g., a speaker), a network interface device 420, and one or more sensors 421, such as a global positioning system (GPS) sensor, compass, accelerometer, or another sensor. The machine 400 may include an output controller 428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 416 may include a machine readable medium 422 on which is stored one or more sets of data structures or instructions 424 (e.g., software) embodying or utilized by any one or more of the techniques or functions described herein. The instructions 424 may also reside, completely or at least partially, within the main memory 404, within static memory 406, or within the hardware processor 402 during execution thereof by the machine 400. In an example, one or any combination of the hardware processor 402, the main memory 404, the static memory 406, or the storage device 416 may constitute machine readable media.

While the machine readable medium 422 is illustrated as a single medium, the term "machine readable medium" may include a single medium or multiple media (e.g., a centralized or distributed database, and/or associated caches and servers) configured to store the one or more instructions 424.

The term "machine readable medium" may include any medium that is capable of storing, encoding, or carrying instructions for execution by the machine 400 and that cause the machine 400 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine-readable medium with a plurality of particles having invariant (e.g., rest) mass. Accordingly, massed machine-readable media are not transitory propagating signals. Specific examples of massed machine-readable media may include: nonvolatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks: magneto-optical disks; and CD-ROM and DVD-ROM disks.

The instructions 424 may further be transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 420 may include one or more physical jacks (e.g., Ethernet, coaxial, or phone jacks) or one or more antennas to connect to the communications network 426. In an example, the network interface device 420 may include a plurality of antennas to communicate wirelessly using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 400, and includes digital or analog communications signals or other intangible medium to facilitate communication of such software.

Various embodiments of the present subject matter may include a hearing assistance device. Hearing assistance devices typically include at least one enclosure or housing, a microphone, hearing assistance device electronics including processing electronics, and a speaker or "receiver." Hearing assistance devices may include a power source, such as a battery. In various embodiments, the battery may be rechargeable. In various embodiments multiple energy sources may be employed. It is understood that in various embodiments the microphone is optional. It is understood that in various embodiments the receiver is optional. It is understood that variations in communications protocols, antenna configurations, and combinations of components may be employed without departing from the scope of the present subject matter. Antenna configurations may vary and may be included within an enclosure for the electronics or be external to an enclosure for the electronics. Thus, the examples set forth herein are intended to be demonstrative and not a limiting or exhaustive depiction of variations.

It is understood that digital hearing aids include a processor. In digital hearing aids with a processor, programmable gains may be employed to adjust the hearing aid output to a wearer's particular hearing impairment. The processor may be a digital signal processor (DSP), microprocessor, microcontroller, other digital logic, or combinations thereof. The processing may be done by a single processor, or may be distributed over different devices. The processing of signals referenced in this application can be performed using the processor or over different devices. Processing may be done in the digital domain, the analog domain, or combinations thereof. Processing may be done using subband processing techniques. Processing may be done using frequency domain or time domain approaches. Some processing may involve both frequency and time domain aspects. For brevity, in some examples, drawings may omit certain blocks that perform frequency synthesis, frequency analysis, analog-to-digital conversion, digital-to-analog conversion, amplification, buffering, and certain types of filtering and processing. In various embodiments the processor is adapted to perform instructions stored in one or more memories, which may or may not be explicitly shown. Diverse types of memory may be used, including volatile and nonvolatile forms of memory. In various embodiments, the processor or other processing devices execute instructions to perform a number of signal processing tasks. Such embodiments may include analog components in communication with the processor to perform signal processing tasks, such as sound reception by a microphone, or playing of sound using a receiver (i.e., in applications where such transducers are used). In various embodiments, different realizations of the block diagrams, circuits, and processes set forth herein can be created by one of skill in the art without departing from the scope of the present subject matter.

Various embodiments of the present subject matter support wireless communications with a hearing assistance device. In various embodiments, the wireless communications can include standard or nonstandard communications. Some examples of standard wireless communications include, but not limited to, Bluetooth™, low energy Bluetooth, IEEE 802.11 (wireless LANs), 802.15 (WPANs), and 802.16 (WiMAX). Cellular communications may include, but not limited to, CDMA, GSM, ZigBee, and ultra-wideband (UWB) technologies. In various embodiments, the communications are radio frequency communications. In various embodiments, the communications are optical communications, such as infrared communications. In various embodiments, the communications are inductive communications. In various embodiments, the communications are ultrasound communications. Although embodiments of the present system may be demonstrated as radio communication systems, it is possible that other forms of wireless communications can be used. It is understood that past and present standards can be used. It is also contemplated that future versions of these standards and new future standards may be employed without departing from the scope of the present subject matter.

The wireless communications support a connection from other devices. Such connections include, but are not limited to, one or more mono or stereo connections or digital connections having link protocols including, but not limited to 802.3 (Ethernet), 802.4, 802.5, USB, ATM, Fiber-channel, Firewire or 1394, InfiniBand, or a native streaming interface. In various embodiments, such connections include all past and present link protocols. It is also contemplated that future versions of these protocols and new protocols may be employed without departing from the scope of the present subject matter.

In various embodiments, the present subject matter is used in hearing assistance devices that are configured to communicate with mobile phones. In such embodiments, the hearing assistance device may be operable to perform one or more of the following: answer incoming calls, hang up on calls, and/or provide two-way telephone communications. In various embodiments, the present subject matter is used in hearing assistance devices configured to communicate with packet-based devices. In various embodiments, the present subject matter includes hearing assistance devices configured to communicate with streaming audio devices. In various embodiments, the present subject matter includes hearing assistance devices configured to communicate with Wi-Fi devices. In various embodiments, the present subject matter includes hearing assistance devices capable of being controlled by remote control devices.

It is further understood that different hearing assistance devices may embody the present subject matter without departing from the scope of the present disclosure. The devices depicted in the figures are intended to demonstrate the subject matter, but not necessarily in a limited, exhaustive, or exclusive sense. It is also understood that the present subject matter can be used with a device designed for use in the right ear or the left ear or both ears of the wearer. The present subject matter may be employed in hearing assistance devices, such as headsets, hearing aids, headphones, and similar hearing devices. The present subject matter may be employed in hearing assistance devices having additional sensors. Such sensors include, but are not limited to, magnetic field sensors, telecoils, temperature sensors, accelerometers, and proximity sensors.

The present subject matter is demonstrated for hearing assistance devices, including hearing aids, including but not limited to, behind-the-ear (BTE), in-the-ear (ITE), in-the-canal (ITC), receiver-in-canal (RIC), or completely-in-the-canal (CIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user, including but not limited to receiver-in-canal (RIC) or receiver-in-the-ear (RITE) designs. The present subject matter can also be used in hearing assistance devices generally, such as cochlear implant type hearing devices and such as deep insertion devices having a transducer, such as a receiver or microphone, whether custom fitted, standard fitted, open fitted and/or occlusive fitted. It is understood that other hearing assistance devices not expressly stated herein may be used in conjunction with the present subject matter.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

Example 1 is a hearing assistance device fitting system, the system comprising: a hearing assistance device; a heart rate sensor supported by the hearing assistance device, the heart rate sensor to generate a heart rate sensor signal of a patient; a memory; and a processor configured to execute instructions to: receive the heart rate sensor signal; determine an incorrect fitting of the hearing assistance device based on the heart rate sensor signal; and generate a notification indicating the incorrect fitting of the hearing assistance device.

In Example 2, the subject matter of Example 1 optionally includes wherein the heart rate sensor signal includes a heart rate indication, wherein the determination of the incorrect fitting is based on a detected irregularity in the heart rate indication.

In Example 3, the subject matter of Example 2 optionally includes wherein the heart rate sensor signal further includes a skin contact flag, wherein the determination of the incorrect fitting is based on a detected insufficient contact in the skin contact flag.

In Example 4, the subject matter of any one or more of Examples 2-3 optionally include wherein the heart rate sensor signal further includes at least one of a signal quality and an optical DC value.

In Example 5, the subject matter of any one or more of Examples 1-4 optionally include wherein: the hearing assistance device includes an in-ear portion; and the heart rate sensor is attached to the in-ear portion.

In Example 6, the subject matter of any one or more of Examples 1-5 optionally include wherein: the hearing assistance device includes a receiver-in-canal cable; and the heart rate sensor is attached to the receiver-in-canal cable.

In Example 7, the subject matter of any one or more of Examples 1-6 optionally include wherein: the hearing assistance device includes an above-ear portion; and the heart rate sensor is attached to the above-ear portion.

In Example 8, the subject matter of any one or more of Examples 1-7 optionally include a transducer to transduce an audible position change instruction to the patient, the audible position change instruction including at least one of a sitting command, a standing command, and a walking command.

In Example 9, the subject matter of Example 8 optionally includes wherein the transducer is further to transduce an audible notification to the patient, the audible notification based on the notification indicating the incorrect fitting of the hearing assistance device.

In Example 10, the subject matter of any one or more of Examples 1-9 optionally include a mobile electronic device external to the hearing assistance device, the mobile electronic device including a device display to display a visual indication of the notification indicating the incorrect fitting of the hearing assistance device.

In Example 11, the subject matter of Example 10 optionally includes a wireless hearing assistance device radio within the hearing assistance device to transmit the heart rate sensor signal to the mobile electronic device.

In Example 12, the subject matter of Example 11 optionally includes wherein the wireless hearing assistance device radio is further to transmit the notification indicating the incorrect fitting of the hearing assistance device to the mobile electronic device.

In Example 13, the subject matter of any one or more of Examples 1-12 optionally include wherein the processor is disposed within the hearing assistance device.

In Example 14, the subject matter of any one or more of Examples 1-13 optionally include wherein the processor is disposed within the mobile electronic device.

Example 15 is a hearing assistance device fitting method, the method comprising: generating a heart rate sensor signal of a patient at a heart rate sensor supported by a hearing assistance device determining an incorrect fitting of the hearing assistance device based on the heart rate sensor signal; and generating a notification indicating the incorrect fitting of the hearing assistance device.

In Example 16, the subject matter of Example 15 optionally includes wherein: the heart rate sensor signal includes a heart rate indication; and the determination of the incorrect fitting is based on a detected irregularity in the heart rate indication.

In Example 17, the subject matter of Example 16 optionally includes wherein: the heart rate sensor signal further includes a skin contact flag; and the determination of the incorrect fitting is based on a detected insufficient contact in the skin contact flag.

In Example 18, the subject matter of any one or more of Examples 16-17 optionally include wherein the heart rate sensor signal further includes at least one of a signal quality and an optical DC value.

In Example 19, the subject matter of any one or more of Examples 15-18 optionally include wherein: the hearing assistance device includes an in-ear portion; and the heart rate sensor is attached to the in-ear portion.

In Example 20, the subject matter of any one or more of Examples 15-19 optionally include wherein: the hearing assistance device includes a receiver-in-canal cable; and the heart rate sensor is attached to the receiver-in-canal cable.

In Example 21, the subject matter of any one or more of Examples 15-20 optionally include wherein: the hearing assistance device includes an above-ear portion; and the heart rate sensor is attached to the above-ear portion.

In Example 22, the subject matter of any one or more of Examples 15-21 optionally include transducing an audible position change instruction to the patient, the audible position change instruction including at least one of a sitting command, a standing command, and a walking command.

In Example 23, the subject matter of Example 22 optionally includes transducing an audible notification to the patient, the audible notification based on the notification indicating the incorrect fitting of the hearing assistance device.

In Example 24, the subject matter of any one or more of Examples 15-23 optionally include displaying, on a device display of a mobile electronic device external to the hearing assistance device, a visual indication of the notification indicating the incorrect fitting of the hearing assistance device.

In Example 25, the subject matter of Example 24 optionally includes transmitting the heart rate sensor signal from the hearing assistance device to the mobile electronic device.

In Example 26, the subject matter of Example 25 optionally includes transmitting the notification indicating the incorrect fitting of the hearing assistance device from the hearing assistance device to the mobile electronic device.

In Example 27, the subject matter of any one or more of Examples 15-26 optionally include wherein the processor is disposed within the hearing assistance device.

In Example 28, the subject matter of any one or more of Examples 15-27 optionally include wherein the processor is disposed within the mobile electronic device.

Example 29 is one or more machine-readable medium including instructions, which when executed by a computing system, cause the computing system to perform any of the methods of Examples 15-28.

Example 30 is an apparatus comprising means for performing any of the methods of Examples 15-28.

Example 31 is at least one non-transitory machine-readable storage medium, comprising a plurality of instructions that, responsive to being executed with processor circuitry of a computer-controlled device, cause the computer-controlled device to: generate a heart rate sensor signal of a patient at a heart rate sensor supported by a hearing assistance device determine an incorrect fitting of the hearing assistance device based on the heart rate sensor signal; and generate a notification indicating the incorrect fitting of the hearing assistance device.

In Example 32, the subject matter of Example 31 optionally includes wherein: the heart rate sensor signal includes a heart rate indication; and the determination of the incorrect fitting is based on a detected irregularity in the heart rate indication.

In Example 33, the subject matter of Example 32 optionally includes wherein: the heart rate sensor signal further includes a skin contact flag; and the determination of the incorrect fitting is based on a detected insufficient contact in the skin contact flag.

In Example 34, the subject matter of any one or more of Examples 32-33 optionally include wherein the heart rate sensor signal further includes at least one of a signal quality and an optical DC value.

In Example 35, the subject matter of any one or more of Examples 31-34 optionally include wherein: the hearing assistance device includes an in-ear portion; and the heart rate sensor is attached to the in-ear portion.

In Example 36, the subject matter of any one or more of Examples 31-35 optionally include wherein: the hearing assistance device includes a receiver-in-canal cable; and the heart rate sensor is attached to the receiver-in-canal cable.

In Example 37, the subject matter of any one or more of Examples 31-36 optionally include wherein: the hearing assistance device includes an above-ear portion; and the heart rate sensor is attached to the above-ear portion.

In Example 38, the subject matter of any one or more of Examples 31-37 optionally include the plurality of instructions further causing the computer-controlled device to transduce an audible position change instruction to the patient, the audible position change instruction including at least one of a sitting command, a standing command, and a walking command.

In Example 39, the subject matter of Example 38 optionally includes the plurality of instructions further causing the computer-controlled device to transduce an audible notification to the patient, the audible notification based on the notification indicating the incorrect fitting of the hearing assistance device.

In Example 40, the subject matter of any one or more of Examples 31-39 optionally include the plurality of instructions further causing the computer-controlled device to display, on a device display of a mobile electronic device external to the hearing assistance device, a visual indication of the notification indicating the incorrect fitting of the hearing assistance device.

In Example 41, the subject matter of Example 40 optionally includes the plurality of instructions further causing the computer-controlled device to transmit the heart rate sensor signal from the hearing assistance device to the mobile electronic device.

In Example 42, the subject matter of Example 41 optionally includes the plurality of instructions further causing the computer-controlled device to transmit the notification indicating the incorrect fitting of the hearing assistance device from the hearing assistance device to the mobile electronic device.

In Example 43, the subject matter of any one or more of Examples 31-42 optionally include wherein the processor is disposed within the hearing assistance device.

In Example 44, the subject matter of any one or more of Examples 31-43 optionally include wherein the processor is disposed within the mobile electronic device.

Example 45 is an audio and data transmission apparatus for hearing assistance devices, the apparatus comprising: means for generating a heart rate sensor signal of a patient at a heart rate sensor supported by a hearing assistance device means for determining an incorrect fitting of the hearing assistance device based on the heart rate sensor signal; and means for generating a notification indicating the incorrect fitting of the hearing assistance device.

In Example 46, the subject matter of Example 45 optionally includes wherein: the heart rate sensor signal includes a heart rate indication; and the means for determination of the incorrect fitting is based on a detected irregularity in the heart rate indication.

In Example 47, the subject matter of Example 46 optionally includes wherein: the heart rate sensor signal further includes a skin contact flag; and the means for determination of the incorrect fitting is based on a detected insufficient contact in the skin contact flag.

In Example 48, the subject matter of any one or more of Examples 46-47 optionally include wherein the heart rate sensor signal further includes at least one of a signal quality and an optical DC value.

In Example 49, the subject matter of any one or more of Examples 45-48 optionally include wherein: the hearing assistance device includes an in-ear portion; and the heart rate sensor is attached to the in-ear portion.

In Example 50, the subject matter of any one or more of Examples 45-49 optionally include wherein: the hearing assistance device includes a receiver-in-canal cable; and the heart rate sensor is attached to the receiver-in-canal cable.

In Example 51, the subject matter of any one or more of Examples 45-50 optionally include wherein: the hearing assistance device includes an above-ear portion; and the heart rate sensor is attached to the above-ear portion.

In Example 52, the subject matter of any one or more of Examples 45-51 optionally include means for transducing an audible position change instruction to the patient, the audible position change instruction including at least one of a sitting command, a standing command, and a walking command.

In Example 53, the subject matter of Example 52 optionally includes means for transducing an audible notification to the patient, the audible notification based on the notification indicating the incorrect fitting of the hearing assistance device.

In Example 54, the subject matter of any one or more of Examples 45-53 optionally include means for displaying, on a device display of a mobile electronic device external to the hearing assistance device, a visual indication of the notification indicating the incorrect fitting of the hearing assistance device.

In Example 55, the subject matter of Example 54 optionally includes means for transmitting the heart rate sensor signal from the hearing assistance device to the mobile electronic device.

In Example 56, the subject matter of Example 55 optionally includes means for transmitting the notification indicating the incorrect fitting of the hearing assistance device from the hearing assistance device to the mobile electronic device.

In Example 57, the subject matter of any one or more of Examples 45-56 optionally include wherein the processor is disposed within the hearing assistance device.

In Example 58, the subject matter of any one or more of Examples 45-57 optionally include wherein the processor is disposed within the mobile electronic device.

Example 59 is one or more non-transitory machine-readable medium including instructions, which when executed by a machine, cause the machine to perform operations of any of the operations of Examples 1-58.

Example 60 is an apparatus comprising means for performing any of the operations of Examples 1-58.

Example 61 is a system to perform the operations of any of the Examples 1-58.

Example 62 is a method to perform the operations of any of the Examples 1-58.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A hearing assistance device fitting system, the system comprising:
   a hearing assistance device;
   a heart rate sensor supported by the hearing assistance device, the heart rate sensor to generate a heart rate sensor signal of a patient;
   a memory; and
   a processor configured to execute instructions to:
      receive the heart rate sensor signal;
      determine an incorrect fitting of the hearing assistance device based on the heart rate sensor signal; and
      generate a notification indicating the incorrect fitting of the hearing assistance device.

2. The system of claim 1, wherein the heart rate sensor signal includes a heart rate indication, wherein the determination of the incorrect fitting is based on a detected irregularity in the heart rate indication.

3. The system of claim 2, wherein the heart rate sensor signal further includes a skin contact flag, wherein the determination of the incorrect fitting is based on a detected insufficient contact in the skin contact flag.

4. The system of claim 2, wherein the heart rate sensor signal further includes at least one of a signal quality and an optical DC value.

5. The system of claim 1, wherein:
the hearing assistance device includes a receiver-in-canal cable; and
the heart rate sensor is attached to the receiver-in-canal cable.

6. The system of claim 1, further including a transducer to transduce an audible position change instruction to the patient, the audible position change instruction including at least one of a sitting command, a standing command, and a walking command.

7. The system of claim 6, wherein the transducer is further to transduce an audible notification to the patient, the audible notification based on the notification indicating the incorrect fitting of the hearing assistance device.

8. The system of claim 1, further including a mobile electronic device external to the hearing assistance device, the mobile electronic device including a device display to display a visual indication of the notification indicating the incorrect fitting of the hearing assistance device.

9. The system of claim 8, further including a wireless hearing assistance device radio within the hearing assistance device to transmit the heart rate sensor signal to the mobile electronic device.

10. A hearing assistance device fitting method, the method comprising:
generating a heart rate sensor signal of a patient at a heart rate sensor supported by a hearing assistance device;
determining an incorrect fitting of the hearing assistance device based on the heart rate sensor signal; and
generating a notification indicating the incorrect fitting of the hearing assistance device.

11. The method of claim 10, wherein:
the heart rate sensor signal includes a heart rate indication; and
the determination of the incorrect fitting is based on a detected irregularity in the heart rate indication.

12. The method of claim 11, wherein:
the heart rate sensor signal further includes a skin contact flag; and
the determination of the incorrect fitting is based on a detected insufficient contact in the skin contact flag.

13. The method of claim 11, wherein the heart rate sensor signal further includes at least one of a signal quality and an optical DC value.

14. The method of claim 10, wherein:
the hearing assistance device includes a receiver-in-canal cable; and
the heart rate sensor is attached to the receiver-in-canal cable.

15. The method of claim 10, further including transducing an audible position change instruction to the patient, the audible position change instruction including at least one of a sitting command, a standing command, and a walking command.

16. The method of claim 15, further including transducing an audible notification to the patient, the audible notification based on the notification indicating the incorrect fitting of the hearing assistance device.

17. The method of claim 10, further including displaying, on a device display of a mobile electronic device external to the hearing assistance device, a visual indication of the notification indicating the incorrect fitting of the hearing assistance device.

18. The method of claim 17, further including transmitting the heart rate sensor signal from the hearing assistance device to the mobile electronic device.

19. At least one non-transitory machine-readable storage medium, comprising a plurality of instructions that, responsive to being executed with processor circuitry of a computer-controlled device, cause the computer-controlled device to:
generate a heart rate sensor signal of a patient at a heart rate sensor supported by a hearing assistance device;
determine an incorrect fitting of the hearing assistance device based on the heart rate sensor signal; and
generate a notification indicating the incorrect fitting of the hearing assistance device.

20. The non-transitory machine-readable medium of claim 19, wherein:
the heart rate sensor signal includes a heart rate indication; and
the determination of the incorrect fitting is based on a detected irregularity in the heart rate indication.

* * * * *